United States Patent [19]

Omura et al.

[11] 4,440,759
[45] Apr. 3, 1984

[54] 20-AMINO TYLOSIN DERIVATIVES AND PHARMACEUTICAL COMPOSITIONS CONTAINING SAME

[76] Inventors: Satoshi Omura, 12-7 Seta 5-chome, Setagaya-ku, Tokyo; Akira Nakagawa, 30-31 Sumiyoshi-cho 2-chome, Fuchu-Shi, Tokyo, both of Japan

[21] Appl. No.: 469,535

[22] Filed: Feb. 24, 1983

[30] Foreign Application Priority Data

Feb. 25, 1982 [JP] Japan .................................. 57-29480

[51] Int. Cl.$^3$ ...................... A61K 31/71; C07H 15/08
[52] U.S. Cl. ..................................... 424/180; 536/7.1
[58] Field of Search .......................... 424/180; 536/7.1

[56] References Cited

U.S. PATENT DOCUMENTS

| | | | |
|---|---|---|---|
| 3,178,341 | 4/1965 | Hamill et al. | 435/896 X |
| 4,196,280 | 4/1980 | Umezawa et al. | 536/17 R |
| 4,279,896 | 7/1981 | Ganguly et al. | 424/180 |
| 4,345,069 | 8/1982 | Sakakibara et al. | 536/7.1 |

OTHER PUBLICATIONS

H. Matsubara et al., "Chemical Transformation of Tylosin, a 16-Membered Macrolide, and Its Structure–Activity Relationship", *Chem. Pharm. Bull.* 30 (1), 97–110 (1982).

S. Omura et al., "Novel Dimeric Derivatives of Leucomycins and Tylosin, Sixteen-Membered Macrolides", *J. Med. Chem.* 25, 271–275 (1982).

Derwent Abstract No. 71396Y of Japanese Unexamined Patent 2100–485 (Takeda), Aug. 23, 1977.

S. Satoi et al., "Mycinamicins, New Macrolide Antibiotics. I: Taxonomy, Production, Isolation Characterization and Properties", *J. Antibiotics* 33 (4), 364–377, (1980).

Derwent Abstract No. 92092A/51 of Japanese Unexamined Patent 3130–686 (Toyo Brewing), Nov. 14, 1978.

Derwent Abstract No. 008688/01 of Japanese Unexamined Patent 3132–584 (Toyo Brewing) Nov. 18, 1978.

Derwent Abstract No. 65537B/36 of Japanese Unexamined Patent 4095–584 (Toyo Brewing) Jul. 28, 1979.

*Primary Examiner*—Johnnie R. Brown
*Attorney, Agent, or Firm*—Nancy J. Harrison; Arthur R. Whale

[57] ABSTRACT

20-Amino derivatives of tylosin and desmycosin are active against bacteria and Mycoplasma.

10 Claims, No Drawings

20-AMINO TYLOSIN DERIVATIVES AND PHARMACEUTICAL COMPOSITIONS CONTAINING SAME

SUMMARY OF THE INVENTION

Novel macrolides of formula (I):

[Chemical structure of formula (I)]

where R is mycinosyloxy;
where Q is hydrogen or mycarosyl;
where X is a group of formula:

$$-N\diagup^{R^{10}}_{\diagdown R^{11}}$$

where:
(i) $R^{10}$ and $R^{11}$ independently represent $C_{1-4}$ alkyl, $C_{3-10}$ cycloalkyl; or a group of formula:

$$-(CH_2)_n-Ph$$

where n is 0, 1 or 2, and Ph is phenyl optionally substituted by a $C_{1-4}$ alkoxycarbonyl, amino, halogen, $C_{1-4}$ alkyl or $C_{1-4}$ alkoxy group;

(ii) one only of $R^{10}$ and $R^{11}$ represents hydrogen or a group of formula:

[Piperazine ring structure: $-N$ ring $N-R^{12}$]

where $R^{12}$ is hydrogen or $C_{1-4}$ alkyl; or
(iii) $R^{10}$ and $R^{11}$ taken together with the adjacent nitrogen atom, form a heterocyclic ring containing from 5 to 7 ring atoms and including as a further heteroatom oxygen or nitrogen;
or a pharmaceutically-acceptable salt or acyl ester thereof, are useful new antibiotics. Methods of treating infections with, and compositions comprising, the formula I compounds are provided.

DETAILED DESCRIPTION OF THE INVENTION

This invention relates to macrolide antibiotics, in particular to novel compounds similar to the well-known therapeutic agent tylosin (see, for example, *Tetrahedron Letters*, 2339 (1970) and U.S. Pat. No. 3,178,341) but in which the C-20 position of the macrolide system is substituted by an amino function.

Despite tylosin's great value, there exists a continuing need to develop new antibiotics, both in view of the possibility of providing more active derivatives, possibly having a broader spectrum of activity, and also in view of the known propensity of microorganisms to develop resistance. Unfortunately, chemical modification of tylosin-like macrolides has proven to be extremely difficult. Indeed, in the majority of cases, research workers, intent on finding new derivatives of this type, have been forced to search for new microorganisms, in the hope that their cultivation would fortuitously yield related compounds of interest.

Surprisingly, we have now discovered that the C-20 aldehyde group in tylosin-like structures can be converted, via reductive amination, into a C-20 amino function, without concomitant disruption of the macrolide system, and further that such derivatives possess significant antibiotic activity.

Thus, in accordance with the invention, novel macrolides of formula (I):

[Chemical structure of formula (I) with numbered positions]

where R is mycinosyloxy,
where Q is hydrogen or mycarosyl,
where X is a group of formula:

$$-N\diagup^{R^{10}}_{\diagdown R^{11}}$$

where:
(i) $R^{10}$ and $R^{11}$ independently represent $C_{1-4}$ alkyl, $C_{3-10}$ cycloalkyl; or a group of formula:

$$-(CH_2)_n-Ph$$

where n is 0, 1 or 2, and pH is phenyl optionally substitut (ii) one only of $R^{10}$ and $R^{11}$ represents hydrogen or a group of formula:

[Piperazine ring structure: $-N$ ring $N-R^{12}$]

where R[12] is hydrogen or C[1-4] alkyl; or (iii) R[10] and R[11] taken together with the adjacent nitrogen atom, form a heterocyclic ring containing from 5 to 7 ring atoms and including as a further heteroatom oxygen or nitrogen;
and their pharmaceutically-acceptable salts and acyl esters, are effective antibiotics.

Although no stereochemical configuration is indicated in the above structural formula, it is to be understood that the stereochemistry is identical to that of tylosin. The amino sugar is mycaminose.

The term "C$_{3-10}$ cycloalkyl" as used herein refers to carbocyclic groups containing from 3 to 10 carbon atoms, and includes such groups as cyclobutyl, cyclohexyl, cyclooctyl and adamantyl. Similarly, the term "C$_{1-4}$ alkyl" group refers to straight or branched alkyl groups containing from 1 to 4 carbon atoms and includes such groups as methyl, ethyl, n-propyl and i-propyl.

Compounds of formula (I) in which Q is hydrogen are preferred.

When R[10] and R[11] combine to form a heterocyclic ring containing from 5 to 7 ring atoms and including as a further heteroatom oxygen or nitrogen, typical examples of such groups are piperazino and morpholino. It should be understood that the heterocyclic ring must contain two heteroatoms. The heterocyclic ring is preferably saturated.

A further class of compounds of interest which may be mentioned are those wherein X represents a group selected from amino, dimethylamino, anilino, N-methylanilino, o-ethoxycarbonylanilino, benzylamino, aminobenzylamino, halobenzylamino, cyclohexylamino and morpholino.

Presently preferred compounds of the invention are:
20-deoxo-20-(N-methylanilino)tylosin,
20-deoxo-20-(N-benzylamino)demycarosyltylosin, and
20-deoxo-20-(N-morpholino)demycarosyltylosin and their pharmaceutically-acceptable salts and acyl esters.

The macrolides of formula (I), because of the existence of amino functions at C-20 and C-3', are capable of forming acid-addition salts. Such salts, so long as they are sufficiently non-toxic to be useful in the chemotherapy of warm-blooded animals, i.e. pharmaceutically-acceptable salts, are useful as antibiotics in accordance with the invention.

Representative salts of this type include those salts formed by standard reactions with both organic acid and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic and cinnamic acids.

The pharmaceutically-acceptable acyl esters of the invention are preferably those derived from a monocarboxylic acid having from 2 to 7 carbon atoms, such as acetic, propionic, butyric or i-valeric acid.

The compounds of formula (I) can be prepared by the reductive amination of an aldehyde of formula (II):

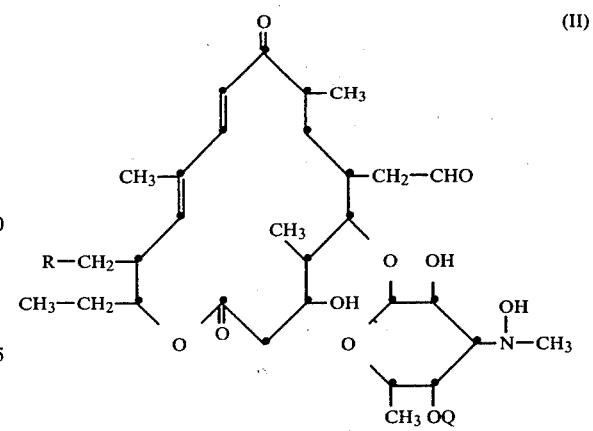

where R and Q are as previously defined, using an aminating agent of formula (III):

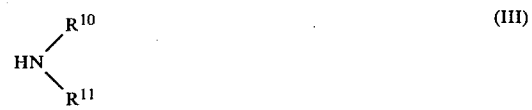

where R[10] and R[11] are as previously defined, or an acid-addition salt thereof.

The reductive amination is preferably accomplished using a cyanoborohydride of formula MBH$_3$CN, where M is a group IA metal or ammonium; sodium cyanoborohydride being the reagent of choice.

The solvent for the reaction will normally be an inert polar organic solvent such as a C$_{1-4}$ alkanol, preferably methanol. Typical reaction temperatures for the reaction will vary from 0° to 60° C., with temperatures of from 20° to 40° C. being preferred. The reaction should normally be effected under neutral conditions (pH 6 to 8).

The reaction is preferably conducted using an excess of the reagent of formula (III), typically from 2 to 3 equivalents. Dehydrating agents such as 4 A molecular sieve or anhydrous sodium or magnesium sulfate can also advantageously be used in the reaction.

Alternatively, the reductive amination can be effected by reduction of the C-20 aldehyde function to the corresponding C-20 hydroxymethyl derivative. That hydroxymethyl group can then be appropriately modified to a group of formula —CH$_2$L, where L is a leaving group capable of undergoing nucleophilic displacement by the aminating agent of formula (III). For instance, in one method the C-20 hydroxyl group can be converted to a trifluoromethanesulfonyl (triflate) group, which may, if desired, be further converted to an iodo radical. In a second method, the iodo derivative can be formed directly by addition of iodine (dissolved in a suitable solvent such as dimethylformamide) to a solution of the 20-hydroxymethyl derivative and triphenylphosphine under a nitrogen atmosphere.

The leaving group at C-20 (iodo, triflate, etc.) can then be displaced by reaction with the aminating agent in a suitable organic solvent, such as acetonitrile, to yield compounds of formula (I).

Hydrolysis of compounds of formula (I) in which Q is mycarose and/or R is mycinosyloxy can be accomplished using conventional procedures such as those described in U.S. Pat. No. 3,459,853.

For instance, the mycarose sugar can be hydrolytically cleaved at a pH of less than 4, preferably in the range from 0.5 to 2.0, at a temperature in the range of from 0° to 60° C., conveniently at about room temperature. The hydrolysis can be effected using a strong aqueous mineral acid such as hydrochloric or sulfuric acid or a strong organic acid such as p-toluenesulfonic acid.

Similarly, the mycinose sugar entity can be hydrolytically removed, although more drastic conditions are needed and some care must be taken to avoid disruption of the macrolide system. Longer reaction times are needed and the pH should be kept in the range from 1.5 to 2.5. Higher temperatures are also necessary, typically in the range from 80° to 130° C., preferably from 90° C. to the reflux temperature of the reaction mixture. Because of the difficulties involved in cleavage of the mycinose sugar, compounds of formula (I) in which R is hydroxy are best prepared by the reductive amination of a starting material of formula (II) in which R is hydroxy.

If desired, the compounds of formula (I) can be esterified to give acyl ester derivatives by treatment with acylating agents using conventional procedures. Suitable organic solvents for this reaction include pyridine and triethylamine. The acylating agent may be an activated carboxylic acid derivative such as a carboxylic acid anhydride or an acid halide having from 2 to 7 carbon atoms. Similarly, the pharmacetically-acceptable salts of the invention can be prepared by conventional salification methods known per se in the art.

Accordingly, the process for preparing a macrolide of formula (I), or a pharmaceutically-acceptable salt or acyl ester thereof, comprises:

(a) reductively aminating a compound of formula (II) using an aminating agent of formula (III), or an acid-addition salt thereof; or (b) cleaving the mycarose sugar from a macrolide of formula (I) in which Q is mycarose by acid hydrolysis so as to provide a compound of formula (I) in which Q is hydrogen; and (c) if necessary, optionally esterifying and/or salifying a product of reaction (a) or (b).

The aldehydes of formula (II) are known in the literature, as is their preparation, see, for instance, U.S. Pat. No. 3,178,341.

The compounds of the invention are active against gram-positive bacteria, for example *Streptococcus pyogenes*, and against Mycoplasma species. Compounds of formula (I) in which Q is hydrogen are also active against certain gram-negative bacteria such as Pasteurella sp. Further, the compounds of the invention are well-absorbed orally and give good blood levels. Clearly, these properties render them useful in preventing or treating microbial infections of warm-blooded animals. To this end, a chemotherapeutically effective amount of a compound of formula (I) can be administered parenterally or orally to an infected or susceptible warm-blooded animal. The compounds can also be administered by insufflation, i.e. by blowing the compound, in the form of a medicated dust, into an enclosed space or room wherein the animals or poultry are held. The animals or poultry breathe the medicated dust present in the air (the medicated dust is also taken into the body through the eyes a process called intraocular injection) and are thus treated or protected.

The size of the dose necessary to control the infection will vary with the severity of the infection and the age, weight, and condition of the animal being treated. However, the total dose required when parenteral administration is being utilized will normally be in the range of from 1 to 100 mg/kg, preferably from 1 to 50 mg/kg. The dose required for oral administration will generally be in the range of from 1 to 300 mg/kg and preferably will be in the range of from 1 to 100 mg/kg.

In another aspect, this invention relates to formulations useful for the control of infections caused by bacteria and Mycoplasma species. These veterinary formulations comprise as an active ingredient a macrolide of formula (I), or a pharmaceutically-acceptable salt or acyl ester thereof, associated with one or more physiologically-acceptable carriers or vehicles therefor.

Often, the most practical way to administer the compounds is by formulation into the animal's food supply or drinking water. A variety of feeds, including the common dry feeds, liquid feeds, and pelleted feeds, may be used.

The methods of formulating veterinary medicaments into animal feeds are well-known. A preferred method is to make a concentrated premix which in turn is used to prepare medicated feeds. Typical premixes may contain from 1 to 400 grams of active ingredient per kilogram of premix, and may be in either liquid or solid form.

The final formulation of feeds for animals or poultry will depend upon the amount of medicament to be administered. Conventional methods of formulating, mixing, and pelleting feeds may all be used to prepare feeds containing the active ingredient.

Injectable compositions containing the compounds of the invention may be either in suspension or solution form. In the preparation of suitable formulations it will be recognized that, in general, the water solubility of the acid addition salts is greater than that of the free bases. Similarly, bases of formula (I) are more soluble in dilute acids or in acidic solutions than in neutral or basic solutions.

In solution form the compound is dissolved in a physiologically-acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically-acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars are all useful suspending agents.

To further illustrate the invention, and to show how the same may be carried into effect, reference will now be made to the following non-limiting Examples.

EXAMPLE 1

20-Deoxo-20-(N-benzylamino)tylosin

Tylosin (5 g), benzylamine hydrochloride (7.9 g) and sodium cyanoborohydride (1.4 g) were dissolved in methanol (50 ml) and the mixture allowed to react under a nitrogen atmosphere for 5 hours at room temperature. After the reaction was complete, the reaction mixture was poured into a cold, saturated, aqueous sodium bicarbonate solution (500 ml) and extracted with chloroform (3×100 ml). The resultant chloroform layer was dried over anhydrous sodium sulfate and concentrated under reduced pressure to dryness to give crude product. The crude product was purified by column chromatography using silica gel as the stationary phase and as eluent a mixture of chloroform, methanol and concentrated ammonium hydroxide (15:1:0.05) to give the title product (3.8 g) as a yellow product, yield 71%.

Elemental Analysis for $C_{53}H_{86}N_2O_{16}$ (Molecular Weight 1006): Found: C, 64.01; H, 8.58; N, 2.69; O, 24.72. Calc.: C, 63.22; H, 8.55; N, 2.78; O, 25.45.

Melting point: 103.5°–107° C.

Specific rotation: $[\alpha]_D^{29} = -55.8°$ (c=1, methanol).

Ultraviolet absorption spectrum: $\lambda_{max}^{CH_3OH} = 283$ nm ($\epsilon$22,900).

Mass spectrum (m/e): 673, 654, 175, 174, 145, 106, 91.

Similarly prepared were:

EXAMPLE 2

20-Deoxo-20-(N,N-dimethylamino)tylosin

Melting point: 119.2°–120.3° C.

$[\alpha]_D^{29}$: −40.4° (c=1, methanol).

Ultraviolet absorption spectrum: $\lambda_{max}^{MeOH}$ ($\epsilon$)=282.5 nm (12,500).

Mass spectrum (m/e): 944, 800, 770, 419, 175.

NMR; δ(ppm): 1.78 (s, $H_{22}$), 2.15 (s, $C_{20}$—N(Me)$_2$), 2.52 (s, $C_{3'}$—N(Me)$_2$), 3.43 (s, $C_{2'''}$—OMe), 3.60 (s, $C_{3'''}$—OMe), 4.23 (d, $H_{1'}$), 4.52 (d, $H_{1'''}$), 4.92 (bt, $H_{15}$), 5.05 (d, $H_{1''}$), 5.90 (d, $H_{13}$), 6.26 (d, $H_{10}$), 7.33 (d, $H_{11}$).

Yield: 84%.

EXAMPLE 3

20-Deoxo-20-(N-anilino)tylosin

Melting point: 111°–113° C.

$[\alpha]_D^{29}$: −86.0° (c=1, methanol).

Mass spectrum (m/e): 831, 658, 190, 175, 145.

NMR; δ(ppm): 1.77 (s, $H_{22}$), 2.46 (s, $C_{3'}$—N(Me)$_2$), 3.46 (s, $C_{2'''}$—OMe), 3.56 (s, $C_{3'''}$—OMe), 4.23 (d, $H_{1'}$), 4.54 (d, $H_{1'''}$), 5.04 (d, $H_{1''}$), 4.97 (bt, $H_{15}$), 5.84 (bd, $H_{13}$), 6.23 (d, $H_{10}$), 6.57 (d, o-H-anilino), 6.67 (d, p-H-anilino), 7.10 (d, m-H-anilino), 7.23 (d, $H_{11}$)

Yield: 48%.

EXAMPLE 4

20-Deoxo-20-[N-(o-ethoxycarbonyl)anilino]tylosin

Melting point: 122.5°–124° C.

Ultraviolet absorption spectrum: $\lambda_{max}^{MeOH}$ ($\epsilon$): 282.3 nm (21,300).

Yield: 34%.

EXAMPLE 5

20-Deoxo-20-(N-methylanilino)tylosin

Melting point: 106.5°–109° C.

Mass spectrum (m/e): 1006, 862, 688, 481, 175, 145.

NMR; δ(ppm): 1.79 (s, $H_{22}$), 2.40 (s, $C_{3'}$—N(Me)$_2$), 2.87 (s, $C_{20}$—N—Me), 3.46 (s, $C_{2'''}$—OMe), 3.59 (s, $C_{3'''}$—OMe), 4.27 (d, $H_{1'}$), 4.54 (d, $H_{1'''}$), 5.05 (d, $H_{1''}$), 5.0 (b, $H_{15}$), 5.83 (bd, $H_{13}$), 6.21 (d, $H_{10}$), 6.7 (d, $C_{20}$—N—(o—H and p—H)Ph), 7.27 (d, $H_{11}$), 7.15 (d, $C_{20}$—N—(m—H)Ph)

Yield: 34%.

EXAMPLE 6

20-Deoxo-20-(N,N-dibenzylamino)tylosin

NMR; δ(ppm): 1.78 (s, $H_{22}$), 2.46 (s, $C_{3'}$—N(Me)$_2$), 3.46 (s, $C_{2'''}$—OMe), 3.60 (s, $C_{3'''}$—OMe), 4.57 (d, $H_{1'''}$), 5.88 (bd, $H_{13}$), 6.23 (d, $H_{10}$), 7.3 (benzyl protons).

Yield: 70%.

EXAMPLE 7

20-Deoxo-20-(N-adamantylamino)tylosin

Melting point: 108.5°–110.5° C.

$[\alpha]_D^{29}$: −32.9 (c=1, methanol).

Ultraviolet absorption spectrum: $\lambda_{max}^{MeOH}$ ($\epsilon$): 284 nm (9,800).

Mass spectrum (m/e): 1050 732, 718, 543, 175, 157, 145.

Yield: 82%.

EXAMPLE 8

20-Deoxo-20-(N,N-dibenzylamino)demycarosyltylosin

NMR: δ(ppm): 1.77 (s, $H_{22}$), 2.46 (s, $C_{3'}$—N(Me)$_2$), 3.50 (s, $C_{2'''}$—OMe), 3.60 (s, $C_{3'''}$—OMe), 4.54 (d, $H_{1'}$), 5.06 (bt, $H_{15}$), 5.90 (bd, $H_{13}$), 6.25 (d, $H_{10}$), ca. 7.3 (benzyl proton).

Yield: 95%.

EXAMPLE 9

20-Deoxo-20-(N-cyclohexylamino)tylosin

Melting point: 111°–114° C.

$[\alpha]_D^{29}$: −48.9° (c=1, methanol).

Ultraviolet absorption spectrum: $\lambda_{max}^{MeOH}$ ($\epsilon$): 284 nm (20,000).

Mass spectrum (m/e): 832, 664, 473, 175, 157, 145;

Yield: 50%.

EXAMPLE 10

20-Deoxo-20-(N-benzylamino)demycarosyltylosin

20-Deoxo-20-(N-benzylamino)tylosin (1 g) was dissolved in 0.1 N hydrochloric acid (30 ml) and the mixture was allowed to react at room temperature for 19 hours. After the reaction was complete, the reaction mixture was washed with chloroform (30 ml) and the pH of the resulting aqueous layer was adjusted to 8.0 with 1 N sodium hydroxide. The solution was then extracted with chloroform (3×100 ml), the chloroform layer dried over anhydrous sodium sulfate, and concentrated under reduced pressure to dryness to give 820 mg of a pale yellow, crude material. The crude material was purified by column chromatography using as the stationary phase silica gel and as the eluent a mixture of chloroform, methanol and concentrated ammonium hydroxide (20:1:0.05) to give 620 mg of the title compound as a white material, yield 72%.

Elemental Analysis for $C_{46}H_{74}N_2O_{13}$ (Molecular Weight 862): Found: C, 64.10; H, 8.60; N, 3.20; O, 24.10. Calc.: C, 64.04; H, 8.58; N, 3.25; O, 24.13.

Melting point: 88.5°–91.5° C.

Specific rotation: $[\alpha]_D^{29} = -35.2°$ (c=1, methanol).

Ultraviolet absorption spectrum: $\lambda_{max}^{CH3OH} = 284$ ($\epsilon$22,000).

Infrared absorption spectrum (KBr method): 3440, 2980, 2950, 1710, 1680, 1590, 1460, 1350, 1165, 1090 $cm^{-1}$.

Mass spectrum (m/e): 756, 672, 565, 482, 174, 91

Similarly prepared was:

EXAMPLE 11

20-Deoxo-20-(N-methylanilino)demycarosyltylosin

Melting point: 95.5°–98.5° C.

Ultraviolet absorption spectrum: $\lambda_{Max}^{MeOH}$ ($\epsilon$): 283 nm (20,600).

Mass spectrum (m/e): 862, 688, 190, 174.

NMR, $\delta$(ppm): 1.77 (s, $H_{22}$), 2.49 (s, $C_{3'}$—$N(Me)_2$), 2.87 (s, $C_{20}$—N—Me), 3.46 (s, $C_{2'''}$—OMe), 3.59 (s, $C_{3'''}$—OMe), 4.33 (d, $H_{1'}$), 4.56 (d, $H_{1'}$), 5.00 (dt, $H_{15}$), 5.84 (bd, $H_{13}$), 6.63 (d, $H_{10}$), 6.70 (d, o-H-anilino), 6.73 (d, p-H-anilino), 7.20 (d, m-H-anilino), ca. 7.2 ($H_{11}$)

Yield: 43%.

EXAMPLE 12

20-Deoxo-20-(N-morpholino)tylosin

A solution of tylosin (500 mg), morpholine (480 mg) and sodium cyanoborohydride (130 mg) in methanol (5 ml) was allowed to react at room temperature under a nitrogen atmosphere for 24 hours. After the reaction was complete, the reaction mixture was poured into a cold, aqueous, saturated, sodium bicarbonate solution (150 ml) and then extracted with chloroform (3×80 ml). The resulting chloroform layer was dried over anhydrous sodium sulfate and then concentrated under reduced pressure to dryness to give the title compound as a crude product. This material was purified by silica gel column chromatography using as eluent a chloroform/methanol/concentrated ammonium hydroxide (30/1/0.05) mixture to give 430 mg of the title product as a white material, yield 80%.

Elemental Analysis for $C_{50}H_{86}N_2O_{17}$ (Molecular weight=986): Found: C, 60.80; H, 8.75; N, 2.83; O, 27.62. Calc.: C, 60.85; H, 8.72; N, 2.84; O, 27.59.

Melting point: 122.5°–124.5° C.

Specific rotation: $[\alpha]_D^{31} = -39.6°$ (c=1, methanol).

Ultraviolet absorption spectrum: $\lambda_{max}^{CH3OH} = 283.5$ nm ($\epsilon$19,500).

Similarly prepared was:

EXAMPLE 13

20-Deoxo-20-(4-N-methylpiperazinylamino)tylosin

Melting point: 95.0°–98.0° C.

$[\alpha]_D^{29}$: −55.4° (c=1, methanol).

Ultraviolet absorption spectrum: $\lambda_{max}^{MeOH}$ ($\epsilon$)=283 nm (17,700).

Mass spectrum (m/e): 1014, 870, 680, 175, 157, 145.

NMR; $\delta$(ppm): 1.79 (s, $H_{22}$), 2.31 (s, 4—Me), 2.47 (s, $C_{3'}$—$N(Me)_2$), 3.47 (s, $C_{2'''}$—OMe), 3.60 (s, $C_{3'''}$—OMe), 4.27 (d, $H_{1'}$), 4.56 (d, $H_{1'''}$), 5.07 (d, $H_{1''}$), 4.95 (b, $H_{15}$), 5.86 (d, $H_{13}$), 6.26 (d, $H_{10}$), 7.27 (d, $H_{11}$)

Yield: 69%.

EXAMPLE 14

20-Deoxo-20-(N,N-dibenzylamino)demycarosyltylosin

Tylosin (1 g) was dissolved in 0.2 N hydrochloric acid, and the mixture allowed to react at room temperature for 4 hours. After the reaction was complete, the reaction mixture was washed with chloroform (20 ml). The resultant aqueous layer was adjusted to pH 8.0 with 1 N sodium hydroxide and then extracted with chloroform (3×30 ml). After the chloroform layer was dried over anhydrous sodium sulfate, the solution was concentrated to dryness under reduced pressure to give a quantitative amount of a pale yellow product. The crude product (consisting mainly of demycarosyltylosin), dibenzylamine (0.5 ml) and sodium cyanoborohydride (330 mg) were dissolved in methanol (10 ml). The mixture was allowed to react under nitrogen at room temperature for 4 hours. After the reaction was complete, the reaction mixture was poured into a cold, aqueous, saturated, sodium bicarbonate solution (50 ml), and then extracted with chloroform (3×50 ml). The chloroform layer was then dried over anhydrous sodium sulfate and concentrated to dryness under reduced pressure to give a crude product which was purified by silica gel column chromatography using as eluent a mixture of chloroform:methanol:concentrated ammonium hydroxide (25:1:0.05) to give the title compound as a white material (950 mg), yield 95%.

NMR: $\delta$(ppm): 1.77 (s, $H_{22}$), 2.46 (s, $C_{3'}$—$N(Me)_2$), 3.50 (s, $C_{2'''}$—OMe), 3.60 (s, $C_{3'''}$—OMe), 4.54 (d, $H_{1''}$), 5.06 (bt, $H_{15}$), 5.90 (bd, $H_{13}$), 6.25 (d, $H_{10}$), ca. 7.3 (benzyl proton).

Similarly prepared were:

EXAMPLE 15

20-Deoxo-20-(N-cyclohexylamino)demycarosyltylosin

Melting point: 98.5°–103.0° C.

$[\alpha]_D^{29}$: −21.9 (c=1, methanol).

Ultraviolet absorption spectrum: $\lambda_{max}^{MeOH}$ ($\epsilon$): 284 nm (22,400).

Mass spectrum (m/e): 854, 664, 473, 175, 174;

Yield: 93%.

EXAMPLE 16

20-Deoxo-20-(N-morpholino)demycarosyltylosin

Melting point: 108.0°–110.0° C.

Ultraviolet absorption spectrum: $\lambda_{max}^{MeOH}$ ($\epsilon$): 283 nm (19,500).

Mass spectrum (m/e): 842, 824, 669, 477, 461, 174.

Yield: 44%.

The antibacterial activity of a representative selection of the compounds of formula (I) can be seen from the following Table which show the results of a number of minimum inhibitory concentrations (MIC) determined by standard agar-dilution assays (24 hour culture at 37° C.).

TABLE

| | MINIMUM INHIBITORY CONCENTRATION (micrograms/ml) | | | | | | | | | | |
|---|---|---|---|---|---|---|---|---|---|---|---|
| | Example No. | | | | | | | | | | |
| Test Organism | 1 | 2 | 3 | 4 | 5 | 10 | 11 | 12 | 13 | 17 | 18 |
| *Staphylococcus* | 3.12 | 12.5 | 1.56 | 1.56 | 1.56 | 0.4 | 0.4 | 0.78 | 1.56 | 1.56 | 0.4 |

TABLE-continued

| | MINIMUM INHIBITORY CONCENTRATION (micrograms/ml) | | | | | | | | | |
|---|---|---|---|---|---|---|---|---|---|---|
| | Example No. | | | | | | | | | |
| Test Organism | 1 | 2 | 3 | 4 | 5 | 10 | 11 | 12 | 13 | 17 | 18 |
| *aureus* FDA 209P | | | | | | | | | | | |
| *Bacillus subtilis* PCI 219 | 0.2 | 1.56 | 0.2 | 0.2 | 0.4 | 0.4 | 0.4 | <0.1 | 0.4 | 0.78 | 3.12 |
| *Bacillus cereus* IFO 3001 | 0.78 | 3.12 | 0.4 | 0.4 | 0.4 | 0.4 | <0.1 | 0.4 | 0.78 | 0.78 | 0.2 |
| *Micrococcus luteus* PCI 1001 | <0.1 | 0.4 | <0.1 | <0.1 | 0.4 | <0.1 | <0.1 | <0.1 | 0.2 | <0.1 | <0.2 |
| *Mycobacterium smegmatis* ATCC 607 | 6.25 | 50 | 25 | 25 | 25 | 3.12 | 25 | 50 | 100 | 100 | 50 |
| *Escherichia coli* NHJ | >100 | >100 | >100 | 100 | 50 | 25 | >100 | 50 | >100 | 50 | 12.5 |
| *Klebsiella pneumoniae* PCI 602 | >100 | >100 | 50 | 50 | 50 | 50 | 50 | 50 | 100 | 50 | 12.5 |
| *Salmonella typhimurium* KB 20 | >100 | >100 | >100 | >100 | 100 | 50 | >100 | 100 | 100 | 100 | 100 |

Further, it is also worthy of note that 20-deoxo-20-(N-benzylamino)demycarosyltylosin, when administered orally to mice infected with *Streptococcus pyogenes*, exhibited an ED$_{50}$ (effective dose for protecting 50% of the test animals) of 39 mg/kg, indicating an activity almost twice that of demycarosyltylosin.

I claim:

1. A macrolide of formula (I):

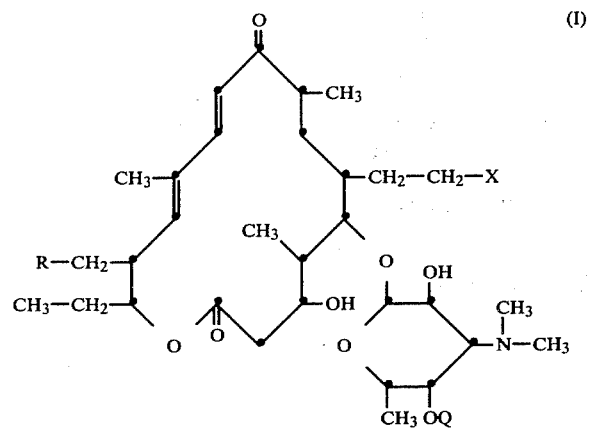

where R is mycinosyloxy,
where Q is hydrogen or mycarosyl,
where X is a group of formula:

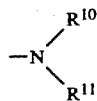

where:
(i) $R^{10}$ and $R^{11}$ independently represent $C_{1-4}$ alkyl, $C_{3-10}$ cycloalkyl; or a group of formula:

$$-(CH_2)_n-Ph$$

where n is 0, 1 or 2, and Ph is phenyl or phenyl substituted by a $C_{1-4}$ alkoxycarbonyl, amino, halogen, $C_{1-4}$ alkyl or $C_{1-4}$ alkoxy group;
(ii) one only of $R^{10}$ and $R^{11}$ represents hydrogen or a group of formula:

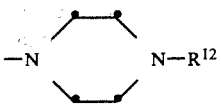

where $R^{12}$ is hydrogen or $C_{1-4}$ alkyl, or
(iii) $R^{10}$ and $R^{11}$ taken together with the adjacent nitrogen atom form a heterocyclic ring selected from piperazino and morpholino; or a pharmaceutically-acceptable salt, or an acyl ester derived from a monocarboxylic acid having from 2 to 7 carbon atoms, thereof.

2. A compound of claim 1 in which Q is hydrogen.

3. A compound of claim 1 in which X represents a group selected from dimethylamino, anilino, N-methylanilino, o-ethoxycarbonylanilino, benzylamino, aminobenzylamino, halobenzylamino, cyclohexylamino and morpholino.

4. The compound of claim 3 which is 20-deoxo-20-(N-methylanilino)tylosin.

5. The compound of claim 3 which is 20-deoxo-20-(N-benzylamino)demycarosyltylosin.

6. The compound of claim 3 which is 20-deoxo-20-(N-morpholino)demycarosyltylosin.

7. A method of suppressing or treating microbial infections caused by gram-positive bacteria or Mycoplasma in a warm-blooded animal which comprises administering to said warm-blooded animal a chemotherapeutically-effective amount of a compound of claim 1.

8. A method of suppressing or treating microbial infections caused by Pasteurella in a warm-blooded animal which comprises administering to said warm-blooded animal a chemotherapeutically-effective amount of a compound of claim 2.

9. A feed premix comprising as an active ingredient an amount of a compound of claim 1 which is effective to suppress or treat microbial infections caused by gram-positive bacteria, Mycoplasma or Pasteurella.

10. A veterinary formulation which comprises as an active ingredient an amount of a compound of claim 1 which is effective to suppress or treat microbial infections caused by gram-positive bacteria, Mycoplasma or Pasteurella associated with one or more physiologically-acceptable carriers or vehicles therefor.

* * * * *